United States Patent
King et al.

(10) Patent No.: US 7,683,133 B2
(45) Date of Patent: Mar. 23, 2010

(54) BEARING MATERIAL OF MEDICAL IMPLANT AND METHODS FOR MAKING IT

(75) Inventors: Richard S. King, Warsaw, IN (US); Craig Ernsberger, Granger, IN (US)

(73) Assignee: DePuy Products, Inc., Warsaw, IN (US)

(*) Notice: Subject to any disclaimer, the term of this patent is extended or adjusted under 35 U.S.C. 154(b) by 0 days.

(21) Appl. No.: 11/844,195

(22) Filed: Aug. 23, 2007

(65) Prior Publication Data

US 2008/0071026 A1 Mar. 20, 2008

Related U.S. Application Data

(60) Provisional application No. 60/840,241, filed on Aug. 25, 2006.

(51) Int. Cl.
C08L 53/00 (2006.01)
C08L 29/00 (2006.01)
C08L 33/02 (2006.01)
C08L 35/00 (2006.01)
B28B 19/00 (2006.01)

(52) U.S. Cl. ............ 525/240; 525/208; 525/222; 525/231; 525/327.2; 264/239; 623/23.58

(58) Field of Classification Search ............... 525/90, 525/69, 208, 223, 240, 326.1, 327.2, 330.3, 525/330.6, 222, 231; 623/23.58; 264/239
See application file for complete search history.

(56) References Cited

U.S. PATENT DOCUMENTS

| | | | |
|---|---|---|---|
| 3,297,805 A | 1/1967 | Rottig et al. | |
| 3,954,927 A | 5/1976 | Duling et al. | |
| 4,454,612 A | 6/1984 | McDaniel et al. | |
| 4,670,508 A | 6/1987 | Ohdaira et al. | |
| 4,778,601 A | 10/1988 | Lopatin et al. | |
| 4,880,843 A | 11/1989 | Stein | |
| 5,275,838 A | 1/1994 | Merrill | |
| 5,288,818 A | 2/1994 | Livingston, Jr. et al. | |
| 5,414,049 A | 5/1995 | Sun et al. | |
| 5,489,303 A | 2/1996 | Sasaki et al. | |
| 5,593,719 A | 1/1997 | Dearnaley et al. | |
| 5,594,055 A | 1/1997 | Young | |
| 5,721,334 A | 2/1998 | Burstein et al. | |
| 5,827,904 A | 10/1998 | Hahn | |
| 5,844,027 A | 12/1998 | Burdick et al. | |
| 5,879,400 A | 3/1999 | Merrill et al. | |
| 5,945,457 A * | 8/1999 | Plate et al. ............ 514/772.1 | |
| 6,017,975 A | 1/2000 | Saum et al. | |
| 6,174,934 B1 | 1/2001 | Sun et al. | |
| 6,228,900 B1 | 5/2001 | Shen et al. | |
| 6,242,507 B1 | 6/2001 | Saum et al. | |
| 6,277,390 B1 | 8/2001 | Schaffner | |
| 6,281,264 B1 | 8/2001 | Salovey et al. | |
| 6,316,158 B1 | 11/2001 | Saum et al. | |
| 6,365,089 B1 | 4/2002 | Krebs et al. | |
| 6,379,741 B1 | 4/2002 | Komvopoulos et al. | |
| 6,395,799 B1 | 5/2002 | Johnson | |
| 6,448,315 B1 | 9/2002 | Lidgren et al. | |
| 6,494,917 B1 | 12/2002 | McKellop et al. | |
| 6,800,670 B2 | 10/2004 | Shen et al. | |
| 6,818,172 B2 | 11/2004 | King et al. | |
| 2002/0125614 A1 | 9/2002 | King et al. | |
| 2003/0083433 A1 | 5/2003 | James et al. | |
| 2003/0125513 A1 | 7/2003 | King | |
| 2003/0144741 A1 | 7/2003 | King et al. | |
| 2003/0144742 A1 | 7/2003 | King et al. | |
| 2003/0149125 A1 | 8/2003 | Muratoglu et al. | |
| 2003/0193110 A1 | 10/2003 | Yaritz et al. | |
| 2003/0212161 A1 | 11/2003 | McKellop et al. | |
| 2004/0156879 A1 | 8/2004 | Muratoglu et al. | |
| 2004/0210316 A1 | 10/2004 | King et al. | |
| 2004/0243249 A1 | 12/2004 | Ishihara et al. | |
| 2004/0262809 A1 | 12/2004 | Smith et al. | |
| 2004/0265165 A1 | 12/2004 | King | |
| 2004/0266903 A1 | 12/2004 | King | |
| 2005/0019366 A1 | 1/2005 | Zeldis | |

(Continued)

FOREIGN PATENT DOCUMENTS

DE 227 328 A1 9/1985

(Continued)

OTHER PUBLICATIONS

European Patent Office, European Search Report in European Patent Application No. 07252847.4 (Mar. 3, 2008).

(Continued)

*Primary Examiner*—Irina S Zemel
*Assistant Examiner*—Jeffrey Lenihan
(74) *Attorney, Agent, or Firm*—Leydig, Voit & Mayer, Ltd.

(57) ABSTRACT

Disclosed is a bearing material of a medical implant, which is an ultrahigh molecular weight polyethylene (UHMWPE) composite. The composite comprises, for example, UHMWPE and a polyethylene copolymer having a polymer backbone and pendant hydrophilic groups or pendant surface active agents that are attached to the polymer backbone. Also disclosed are methods for preparing bearing materials. The bearing material has one or more advantageous properties including reduced immune response, reduced wear, and/or increased lubrication.

20 Claims, No Drawings

U.S. PATENT DOCUMENTS

| | | | |
|---|---|---|---|
| 2005/0065307 | A1 | 3/2005 | King et al. |
| 2005/0069696 | A1 | 3/2005 | King et al. |
| 2006/0004168 | A1 | 1/2006 | Greer et al. |
| 2006/0149387 | A1 | 7/2006 | Smith et al. |
| 2006/0149388 | A1 | 7/2006 | Smith et al. |

FOREIGN PATENT DOCUMENTS

| | | | |
|---|---|---|---|
| EP | 0 047 171 | A2 | 3/1982 |
| EP | 0 335 613 | A2 | 10/1989 |
| EP | 0681845 | A2 | 11/1995 |
| EP | 0 730 001 | A1 | 9/1996 |
| EP | 0 805 178 | A1 | 11/1997 |
| EP | 1 086 709 | A1 | 3/2001 |
| EP | 1 493 775 | A1 | 1/2005 |
| EP | 1520877 | A1 | 4/2005 |
| EP | 1 779 876 | A3 | 5/2007 |
| JP | 48-054168 | A | 7/1973 |
| JP | 60-252645 | A | 12/1985 |
| WO | WO 85/04365 | A1 | 10/1985 |
| WO | WO 86/02656 | A1 | 5/1986 |
| WO | WO 93/25247 | A1 | 12/1993 |
| WO | WO 97/29895 | A1 | 8/1997 |
| WO | WO 00/49079 | A1 | 8/2000 |
| WO | WO 02/26464 | A1 | 4/2002 |
| WO | WO 03/057769 | A1 | 7/2003 |
| WO | WO 03/087217 | A1 | 10/2003 |
| WO | WO 2004/064618 | A | 8/2004 |

OTHER PUBLICATIONS

Zhang et al., "A novel ultra high molecular weight polyethylene-hyaluronan microcomposite for use in total joint replacements. I. Synthesis and physical/chemical characterization," *J. Biomed. Mater. Res. A*, 78A, 86-96 (Apr. 2006).

Barr et al., "EPR as a quality control method for the release of cross-linked ultra high molecular weight polyethylene," *Bruker EPR Application Note*, 1-3 (Bruker Instruments, Inc., Billerica, Massachusetts, Feb. 28, 2003).

Bavaresco et al., "Devices for use as an artificial articular surface in joint prostheses or in the repair of osteochondral defects," *Artificial Organs*, 24 (3): 202-205 (2000).

Beauregard et al., "Synthesis and characterization of a novel UHMWPE interpenetrating polymer network," *Biomedical Sciences Instrumentation*, 35: 415-419 (Apr. 16, 1999).

European Patent Office, Search Report in European Patent Application No. 06255075.1 (Mar. 30, 2007).

King et al., "Hydrophilic, pourous ultra-high molecular weight polyethylene for orthopaedic implants," *Transactions 7th World Biomaterials Congress*, 1909 (May 2004).

Kurtz et al., "Advanced in the processing, sterilization, and crosslinking of ultra-high molecular weight polyethylene for total joint arthroplasty," *Biomaterials*, 20 (18): 1659-1688 (1999).

Oral et al., "α-Tocopherol-doped irradiated UHMWPE for high fatigue resistance and low wear," *Biomaterials*, 25 (24): 5515-5522 (2004).

Shutov et al., "Cellular UHMW polyethylene produced by non-foaming leaching technique: Morphology and properties," *J. Cell. Plast.*, 38: 163-176 (Mar. 2002).

Stein, "Ultra high molecular weight polyethylene (UHMWPE)," *Engineered Materials Handbook vol. 2: Engineering Plastics*, 167-171 (ASM International, Materials park, Ohio, US, 1998).

Veiga-Crespo et al., "Influence of culture conditions of *Gordonia jacobaea* MV-26 on canthaxanthin production," *Int. Microbiol.*, 8 (1): 55-58 (Mar. 2005).

Zhang et al., "Surface modification of UHMWPE for use in total joint replacements," *Biomedical Science Instrumentation*, 40: 13-17 (Apr. 2004).

\* cited by examiner

BEARING MATERIAL OF MEDICAL IMPLANT AND METHODS FOR MAKING IT

CROSS-REFERENCE TO RELATED APPLICATIONS

This patent application claims the benefit of U.S. Provisional Patent Application No. 60/840,241, filed Aug. 25, 2006, which is incorporated by reference.

BACKGROUND OF THE INVENTION

Ultrahigh molecular weight polyethylene ("UHMWPE") is commonly used in making medical or orthopaedic implants, such as artificial hip joints. The implant comprises a bearing material which articulates against a hard counterface such as a metal or ceramic counterpart. UHMWPE, as a bearing material, offers both toughness and abrasion resistance when the bearing material articulates against the hard counterface. In recent years, it has become increasingly apparent that tissue necrosis and osteolysis at the interface of the orthopaedic implant and the host bone are primary contributors to the long-term loosening failure of prosthetic joints. It is generally accepted by orthopaedic surgeons and biomaterials scientists that this tissue necrosis and osteolysis is due, at least in part, to the presence of microscopic particles of UHMWPE produced during the wear of the UHMWPE components. The reaction of the body, e.g., immune response, to these particles includes inflammation and deterioration of the tissues, particularly the bone to which the orthopaedic implant is anchored. Eventually, the orthopaedic implant becomes painful and/or loose and must be revised and/or replaced. There is a desire to improve the orthopaedic implants so that the immune response is reduced or eliminated. The present invention provides such an implant.

BRIEF SUMMARY OF THE INVENTION

The foregoing need is addressed by the invention which provides a bearing material of a medical implant. The bearing material comprises an ultrahigh molecular weight polyethylene (UHMWPE) composite. The bearing material has reduced wear rate and/or elicits reduced or minimal immune response. The composite comprises UHMWPE and a copolymer. For example, the copolymer has a polymer backbone and pendant hydrophilic groups or pendant surface active agents that are attached to the polymer backbone. The present invention also provides methods for preparing a bearing material.

DETAILED DESCRIPTION OF THE INVENTION

The present invention contemplates providing a hydrophilic environment, for example, pendant hydrophilic groups or pendant surface active agents, at the interface between the bearing material and the hard counterface of the implant. It is believed, without wishing to be bound by theory or mechanism, that the hydrophilic environment reduces the immune response of the body. As the bearing material of the invention wears out during use, the hydrophilic particles that are generated may be assimilated by the body and excreted through the kidney. Thus, the microscopic debris coming off the bearing material is not available to macrophages in the body, thereby reducing the possibility of eliciting an adverse immune response. Alternatively, or in addition, the pendant hydrophilic group or the pendant surface active agent reduces friction at the interface between the bearing material and the counterface. Further alternatively, or in addition, the pendant hydrophilic group or the pendant surface active agent alters the interaction of macromolecules found in the physiological fluid, e.g., proteins, with the surface of the bearing material.

Accordingly, in an embodiment, the invention provides a bearing material of a medical implant comprising a composite of an ultrahigh molecular weight polyethylene (UHMWPE) and a polyethylene copolymer having a polymer backbone and pendant hydrophilic groups or pendant surface active agents that are attached to the polymer backbone, wherein the bearing material is adopted for articulating against a hard counterface of the medical implant.

The term "UHMWPE" refers to a polyethylene polymer having a weight average molecular weight of about 400,000 amu or more. Preferably, the E has a weight average molecular weight of about 1,000,000 (e.g., about 2,000,000 or about 3,000,000) amu or more. Typically, the weight average molecular weight of the UHMWPE is about 10,000,000 amu or less, more preferably about 6,000,000 amu or less. UHMWPE suitable for use in the invention includes, but is not limited to, commercially available UHMWPE's such as GUR 1050 and GUR 1020 powdered UHMWPE (weight average molecular weight of about 2,000,000 to about 6,000,000 amu) from Ticona (Summit, N.J.). The UHMWPE may be uncrosslinked or crosslinked.

The hard counterface, which can be, for example, a metallic femoral ball or an acetabular cup for example, can be made of metals such as stainless steel, cobalt chromium alloy, or titanium alloy or of ceramics such as alumina or zirconia.

In accordance with an embodiment of the invention, the pendant hydrophilic groups or pendant surface active agents can be present attached to the polymer backbone directly or through an intervening or linking group. The pendant hydrophilic groups or surface active agents can be present attached to the polymer backbone through covalent, ionic, and/or coordinate bonds, preferably covalent bonds.

The polyethylene copolymer and UHMWPE can be present in the bearing material in any suitable proportions, for example, the polyethylene copolymer can be present in an amount of about 0.1% or more, typically from about 20 to about 80%, preferably from about 30 to about 70%, and more preferably from about 45 to about 65% by weight of the bearing material.

The polyethylene copolymer can have any suitable molecular weight, for example, a weight average molecular weight of about 50,000 amu or more, such as from about 100,000 to about 500,000 amu. The polyethylene copolymer can have any suitable melt viscosity. In an embodiment, the polyethylene copolymer has a melt index equal to or greater than 0.5 g/10 minutes, preferably from 0.5 to about 5 g/10 minutes.

Any suitable hydrophilic group can be present. In accordance with an embodiment, the pendant hydrophilic groups are groups having affinity to water or wetting or to a polar medium, e.g., that can form hydrogen bonds, for example, hydroxyl, carboxyl, keto, aldehydo, amino, amido, ether, and fluoro, or nonionic groups such as hydroxyl groups. Any suitable surface active agent can be present on the polymer backbone, for example, a nonionic surface agent, e.g., a copolymer of polyethylene glycol and polypropylene glycol.

Any suitable linking group can be present. In accordance with embodiments of the invention, the linking group may be selected from the group consisting of carboxy alkyl, carboxy hydroxyalkyl, carboxy hydroxyalkoxy, carboxy alkoxy, and carboxy alkoxyalkyl. In an embodiment, the pendant hydrophilic groups can be present attached to the polymer backbone without a linking group.

The linking group can be provided by a suitable choice of reaction chemistry. For example, a carboxy alkyl group linking a pendant hydroxyl group to the polymer backbone can be produced by reacting a polyethylene copolymer such as polyethylene-co-acrylic acid with ethylene glycol. A carboxy alkoxyalkyl group linking a pendant hydroxyl group to the polymer backbone can be produced by reacting a polyethylene copolymer such as polyethylene-co-acrylic acid with diethylene glycol. A carboxy hydroxyalkyl group linking a pendant hydroxyl group to the polymer backbone can be produced by reacting a polyethylene copolymer such as poly(ethylene-co-glycidyl methacrylate) with a polyol such as ethylene glycol or glycerol. A carboxy hydroxyalkoxy group linking a pendant hydroxyl group to the polymer backbone can be produced by reacting a polyethylene copolymer such as poly(ethylene-co-glycidyl methacrylate) with a polyol such as sorbitol or mannitol.

In accordance with embodiments of the invention, the UHMWPE and the polyethylene copolymer can be intermingled, the polyethylene copolymer can be present as a surface coating, or the polyethylene copolymer may have been imbued into the UHMWPE matrix. In an embodiment where the polyethylene copolymer is a surface coating or layer, the surface coating or layer is free of phosphoryl choline groups. In an embodiment, where the surface coating or layer contains an entanglement of UHMWPE and a polyethylene copolymer, such surface coating or layer is free of polyhydroxy polymers such as polyvinyl alcohol and polyethylene glycol and polycarboxy polymers.

The bearing material in accordance with embodiments of the invention can be prepared by any suitable method. For example, a bearing material having pendant hydrophilic groups or pendant surface active agents can be prepared by blending UHMWPE with a polyethylene copolymer having the required pendant groups.

The pendant groups can be incorporated onto the backbone through reaction between a reactive functional group on a polyethylene copolymer and terminal functional groups of a hydrophilic wetting agents or surface active agents. The reaction can be carried out at a suitable temperature, preferably at elevated temperatures during compression molding, e.g., from about 300 to about 450° F., and more preferably from about 375 to about 425° F.

In accordance with an embodiment of the invention, to prepare a bearing material comprising UHMWPE and a polyethylene copolymer having pendant hydrophilic groups, such as hydroxyl groups, UHMWPE powder can be blended with a polyethylene copolymer having a glycidyl group such as poly(ethylene-co-glycidyl ester) (e.g., poly(ethylene-co-glycidyl methacrylate)) and a polyol (e.g., sorbitol). The polyethylene copolymer and the polyol can be present in any suitable ratio, i.e., the hydroxyl groups of the polyol can be present in a molar ratio less than, equal to, or preferably greater than the glycidyl group of the polyethylene copolymer. The resulting blend is compression molded. The molded product can be machined to the desired size and shape, followed by packaging the product and sterilizing by suitable method. For example, the product can be packaged in a polyethylene package (TYVEK™) and sterilized by a gas plasma or ethylene oxide.

In another embodiment of the invention, to prepare a bearing material comprising UHMWPE and a pendant surface active agent, UHMWPE powder can be blended with a polyethylene copolymer having a pendant carboxyl group such as poly(ethylene-co-acrylic acid) and a polyethylene glycol-polypropylene glycol copolymer (e.g., PLURONIC™ 68). The polyethylene copolymer and the polyethylene glycol-polypropylene glycol copolymer can be present in any suitable ratio, i.e., the hydroxyl groups of the polyethylene glycol-polypropylene glycol copolymer can be present in a molar ratio less than, equal to, or preferably greater than the carboxyl group of the polyethylene copolymer. The resulting blend is compression molded. The resulting product may be packaged in a vacuum foil and optionally crosslinked by gamma irradiation. Any residual free radical present in the product can be reduced or destroyed by melt annealing the product, which is then machined to the desired shape and size. As discussed, the product can be packaged and sterilized.

In another embodiment, copolymers containing blocks or segments of hydrophilic chains (e.g., ethylene glycol, propylene glycol, vinyl alcohol, etc.) can be used. The polyethylene copolymer can be random copolymer, block copolymer or copolymer with polar branches and/or pendants. Any suitable combinations of processes are possible; for example, these can include reacting polyethylene copolymers with wetting agents or surface active agents prior to compression molding, and diffusing and/or reacting wetting agents or surface active agents with molded UHMWPE/polyethylene copolymer prior to crosslinking.

For example, UHMWPE powder can be blended with poly(ethylene-co-ethylene glycol) and the blend is compression molded, followed by vacuum foil packaging, gamma irradiation to crosslink the UHMWPE, melt annealing, machining, packaging in polyethylene and sterilization as discussed above.

In any of the embodiments above, the temperature of compression molding can be from about 300 to about 450° F., preferably from about 350 to about 400° F., and the pressure can be from about 300 psi to about 8,000 psi and preferably from about 500 psi to about 4000 psi. In embodiments, it is preferable to avoid moisture and/or oxygen in view of the sensitivity of one or more materials during compression molding. Accordingly, the compression molding is carried out in an inert environment, for example, under a nitrogen atmosphere, or under reduced pressure.

The residence time of the material in compression molding can be from about 5 to about 30 minutes and preferably from about 10 to about 20 minutes depending, for example, upon the desired thickness of the bearing material. In a two-step process, for example, wherein a consolidated UHMWPE material is molded first followed by laminating the copolymer bearing hydrophilic groups or surface active agents, the processing conditions of the two steps could be different, for example, they may require different temperatures, pressures, and/or shear.

Crosslinking of the UHMWPE can be accomplished by any suitable method, for example, irradiation with X-ray, gamma ray, or e-beam, or microwave or ultrasonic waves.

The bearing material of the invention can have any suitable thickness. In an embodiment where the bearing material is used as a liner of an implant, the thickness can be about 3 mm or more, for example, from about 3 mm to about 30 mm. In some embodiments, the thickness is from about 6 mm to about 28 mm, and in other embodiments, the thickness is from about 8 mm to about 20 mm. If the bearing material itself is used as an implant, the thickness can be about 3 mm or more, for example, from about 3 mm to about 30 mm. In some embodiments, the thickness is from about 6 mm to about 28 mm, and in other embodiments, the thickness is from about 8 mm to about 25 mm.

It is contemplated that the bearing material of the invention can have a number of uses. For example, the bearing material can be a prosthetic acetabular cup, an insert or liner of the acetabular cup, a trunnion bearing or a component thereof, a prosthetic tibial plateau, a patellar button, a prosthetic talar surface, a prosthetic radio-humeral joint, an ulno-humeral joint, a glenoro-humeral articulation, an intervertebral disk replacement, a facet joint replacement, a temporo-mandibular joint, or a finger joint. The bearing material can be a liner for the acetabular component of a hip arthroplasty or the tibial bearing for a knee arthroplasty.

The bearing material or implant of the invention, can find use as a prosthesis for any suitable part of the body, e.g., such as a component of a joint in the body. For example, in a hip joint, the bearing material or implant can be a prosthetic acetabular cup, or the insert or liner of the cup, or a component of a trunnion bearing (e.g., between the modular head and the stem). In a knee joint, the bearing material or implant can be a prosthetic tibial plateau (femoro-tibial articulation), a patellar button (patello-femoral articulation), a trunnion or other bearing component, depending on the design of the artificial knee joint. For example, in a knee joint of the meniscal bearing type, both the upper and lower surfaces of the orthopaedic bearing material or implant, i.e., those surfaces that articulate against metallic or ceramic surfaces, may be surface-crosslinked. In an ankle joint, the bearing material or implant can be the prosthetic talar surface (tibio-talar articulation) or other bearing component. In an elbow joint, the bearing material or implant can be the prosthetic radio-humeral joint, the ulno-humeral joint, or other bearing component. In a shoulder joint, the bearing material or implant can be used in the glenoro-humeral articulation. In the spine, the bearing material or implant can be used in intervertebral disk replacement or facet joint replacement. The bearing material or implant can also be made into a temporo-mandibular joint (jaw) or a finger joint. The bearing material can find use as an implant in any part of a body, such as the hip, knee, and extremities.

The invention also provides a process for producing a bearing material of a medical implant comprising a composite of an ultrahigh molecular weight polyethylene (UHMWPE) and a polyethylene copolymer having a polymer backbone and pendant hydrophilic groups or pendant surface active agents that are attached to the polymer backbone, the process comprising: (i) compression molding a mixture comprising an ultrahigh molecular weight polyethylene (UHMWPE), a polyethylene copolymer having a reactive group capable of reacting with a hydroxy group, and a polyol or a surface active agent having a hydroxy group to obtain a molded product; and (ii) machining the molded product to obtain the bearing material.

As discussed, the reactive group of the polyethylene copolymer can be selected from the group consisting of carboxyl, glycidyl, and carboxy anhydride. In an embodiment, the reactive group is selected from the group consisting of carboxyl, glycidyl, and carboxy anhydride and the hydrophilic group is hydroxyl. Examples of a polyethylene copolymer is poly(ethylene-co-glycidyl methacrylate) or poly(ethylene-co-acrylic acid). Examples of polyol include ethylene glycol, propanediols, butanediols, glycerol, pentaerythritol, trimethylolpropane, sorbitol, mannitol, diglycerin, and triglycerin or a polyether polyol, e.g., a block copolymer of ethylene oxide and propylene oxide, the block copolymer having hydroxyl chain ends.

In accordance with another embodiment, the invention provides a process for producing a bearing material of a medical implant comprising a composite of an ultrahigh molecular weight polyethylene (UHMWPE) and a polyethylene copolymer having a polymer backbone and pendant hydrophilic groups or pendant surface active agents attached to the polymer backbone, the process comprising: (i) compression molding a mixture comprising an ultrahigh molecular weight polyethylene (UHMWPE) and a block copolymer comprising polyethylene segments and hydrophilic segments having pendant groups to obtain a molded product; and (ii) optionally machining the molded product to obtain the bearing material.

In an embodiment of the above process, the hydrophilic segments comprise hydroxyl groups. In another embodiment, the block copolymer is poly(ethylene-co-ethylene glycol).

In accordance with yet another embodiment, the invention provides a process for producing a bearing material of a medical implant comprising a composite of an ultrahigh molecular weight polyethylene (UHMWPE) and a polyethylene copolymer having a polymer backbone and pendant hydrophilic groups or pendant surface active agents that are attached to the polymer backbone, the process comprising: (i) compression molding an ultrahigh molecular weight polyethylene (UHMWPE) powder to obtain a consolidated UHMWPE material; (ii) compressing, in contact with the consolidated UHMWPE material, a mixture comprising a polyethylene copolymer having a reactive group capable of reacting with a hydroxy group, and a polyol or a surface active agent having a hydroxy group to obtain a composite; and (iii) optionally machining the compression molded product to obtain the bearing material.

In another embodiment, invention provides a process for producing a bearing material of a medical implant comprising a composite of an ultrahigh molecular weight polyethylene (UHMWPE) and a polyethylene copolymer having a polymer backbone and pendant hydrophilic groups or pendant surface agents attached to the polymer backbone, the process comprising: (i) providing a consolidated UHMWPE material and (ii) compression molding a polyethylene copolymer having a reactive group capable of reacting with hydroxy group, and a polyol or a surface active agent having a hydroxy group in contact with the consolidated UHMWPE material to obtain a composite; and (iii) optionally machining the compression molded product to obtain the bearing material. The molded product can be machined to the desired shape and size prior to compression molding or the product after compression molding can be desirably machined.

In yet another embodiment, the invention provides a process for producing a bearing material of a medical implant comprising a composite of an ultrahigh molecular weight polyethylene (UHMWPE) and a block copolymer having a polymer backbone and pendant hydrophilic groups attached to the polymer backbone, the process comprising: (i) compression molding an ultrahigh molecular weight polyethylene (UHMWPE) powder to obtain a consolidated UHMWPE material; (ii) compressing, in contact with the consolidated UHMWPE material, a block copolymer comprising polyethylene segments and hydrophilic segments having reactive hydrophilic pendant groups to obtain a molded product; and (iii) optionally machining the compression molded product to obtain the bearing material.

In a further embodiment, the invention provides a process for producing a bearing material of a medical implant comprising a composite of an ultrahigh molecular weight polyethylene (UHMWPE) and a block copolymer having a polymer backbone and pendant hydrophilic groups attached to the polymer backbone, the process comprising: (i) providing a consolidated UHMWPE material; and (ii) compressing, in contact with the consolidated UHMWPE material, a block copolymer comprising polyethylene segments and hydrophilic segments having reactive hydrophilic pendant groups to obtain a molded product; and (iii) optionally machining the compression molded product to obtain the bearing material.

In any of the embodiments of the invention, the process of preparing the bearing material may further include crosslinking the UHMWPE, sterilizing the bearing material, and/or melt-annealing the molded product prior to machining.

In any of the embodiments above, the consolidated UHMWPE material is a precursor to the bearing material, which can be of any consolidated shape, e.g., a rod, sheet, preform, or a finished part. The consolidated material can be prepared by any suitable method, for example, by molding, extrusion, or solvent casting. Alternatively, the consolidated UHMWPE material can be machined or molded from a block or sheet of a polymer, e.g., of a crosslinkable polymer such as UHMWPE.

The invention also provides bearing material produced by the above embodiments of the process. The bearing material of the present invention elicits reduced immune system response. In addition, the UHMWPE wear rate is reduced through lubrication effect derived from beneficial interactions between serum proteins and pendant hydrophilic or wetting agents or surface active agents. Permanent anchoring of the hydrophilic groups or surface active agents in the UHMWPE matrix provides performance stability and reliability. An advantage of the invention is that it permits tailoring of surface and/or bulk of the bearing material in regards to wetting and lubrication effects. In embodiments, the present invention provides less expensive processes to produce bearing material. It seeks to avoid multi-stage grafting and/or chemical reactions.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A bearing material of a medical implant comprising a composite of an ultrahigh molecular weight polyethylene (UHMWPE) and a polyethylene copolymer having a polymer backbone and pendant hydrophilic groups or pendant surface active agents that are attached to the polymer backbone, wherein the bearing material is adopted for articulating against a hard counterface of the medical implant, wherein the polyethylene copolymer is poly(ethylene-co-glycidyl methacrylate).

2. The bearing material of claim 1, wherein the polyethylene copolymer has a pendant surface active agent attached to the polymer backbone.

3. The bearing material of claim 2, wherein the UHMWPE is crosslinked.

4. The bearing material of claim 2, wherein the pendant surface active agents comprise a copolymer of polyethylene glycol and polypropylene glycol.

5. A process for producing a bearing material of a medical implant according to claim 1 comprising a composite of an ultrahigh molecular weight polyethylene (UHMWPE) and a polyethylene copolymer having a polymer backbone and pendant hydrophilic groups or pendant surface active agents that are attached to the polymer backbone, the process comprising:
   (i) compression molding a mixture comprising an ultrahigh molecular weight polyethylene (UHMWPE), a polyethylene copolymer which is poly(ethylene-co-glycidyl methacrylate) and a polyol or a surface active agent having a hydrophilic group to obtain a molded product; and
   (ii) machining the molded product to obtain the bearing material.

6. The process of claim 5, wherein the polyol is a polyether polyol.

7. The process of claim 6, wherein the polyether polyol is a block copolymer of ethylene oxide and propylene oxide, said block copolymer having hydroxyl chain ends.

8. The process of claim 5, further comprising crosslinking the UHMWPE.

9. The process of claim 5, which includes optionally sterilizing the bearing material.

10. The process of claim 5, which includes optionally melt-annealing the molded product prior to machining.

11. A bearing material of a medical implant comprising a composite of an ultrahigh molecular weight polyethylene (UHMWPE) and a polyethylene copolymer having a polymer backbone and pendant hydrophilic groups or pendant surface active agents that are attached to the polymer backbone, wherein the bearing material is adopted for articulating against a hard counterface of the medical implant produced by a process comprising:
   (i) compression molding a mixture comprising an ultrahigh molecular weight polyethylene (UHMWPE), a polyethylene copolymer which is poly(ethylene-co-glycidyl methacrylate) and a surface active agent having a hydrophilic group to obtain a molded product; and
   (ii) machining the molded product to obtain the bearing material.

12. A process for producing a bearing material of a medical implant according to claim 1 comprising a composite of an ultrahigh molecular weight polyethylene (UHMWPE) and a polyethylene copolymer having a polymer backbone and pendant hydrophilic groups or pendant surface active agents that are attached to the polymer backbone, the process comprising:

(i) compression molding an ultrahigh molecular weight polyethylene (UHMWPE) powder to obtain a consolidated UHMWPE material;

(ii) compressing, in contact with the consolidated UHMWPE material, a mixture comprising a polyethylene copolymer which is poly(ethylene-co-glycidyl methacrylate) and a polyol or a surface active agent having a hydroxy group to obtain a composite; and (iii) optionally machining the compression molded product to obtain the bearing material.

13. A process for producing a bearing material of a medical implant according to claim 1 comprising a composite of an ultrahigh molecular weight polyethylene (UHMWPE) and a polyethylene copolymer having a polymer backbone and pendant hydrophilic groups or pendant surface active agents that are attached to the polymer backbone, the process comprising:

(i) providing a consolidated UHMWPE material; and (ii) compression molding a polyethylene copolymer which is poly(ethylene-co-glycidyl methacrylate) and a polyol or a surface active agent having a hydroxy group in contact with the consolidated UHMWPE material to obtain a composite; and (iii) optionally machining the compression molded product to obtain the bearing material.

14. The bearing material of claim 1, wherein the UHMWPE is crosslinked.

15. The bearing material of claim 2, wherein the polyethylene copolymer is present in an amount of about 0.1% or more by weight of the bearing material.

16. The bearing material of claim 15, wherein the polyethylene copolymer is present in an amount of about 20% to about 80% by weight of the bearing material.

17. The bearing material of claim 2, wherein the polyethylene copolymer has a weight average molecular weight of about 50,000 amu or more.

18. The bearing material of claim 17, wherein the polyethylene copolymer has a weight average molecular weight of about 100,000 amu to about 500,000 amu.

19. The bearing material of claim 17, wherein the UHMWPE is crosslinked.

20. The bearing material of claim 18, wherein the UHMWPE is crosslinked.

\* \* \* \* \*